United States Patent
Tommy et al.

(10) Patent No.: US 11,051,756 B2
(45) Date of Patent: Jul. 6, 2021

(54) SYSTEM AND METHOD FOR ANALYZING USER'S ACTIVITIES ON CONDUCTIVE FABRICS TO TRIGGER IOT DEVICES

(71) Applicant: Tata Consultancy Services Limited, Mumbai (IN)

(72) Inventors: Robin Tommy, Thiruvananthapuram (IN); Jithin Lr, Thiruvananthapuram (IN)

(73) Assignee: Tata Consultancy Services Limited, Mumbai (IN)

( * ) Notice: Subject to any disclaimer, the term of this patent is extended or adjusted under 35 U.S.C. 154(b) by 0 days.

(21) Appl. No.: 16/687,489

(22) Filed: Nov. 18, 2019

(65) Prior Publication Data

US 2020/0155068 A1 May 21, 2020

(30) Foreign Application Priority Data

Nov. 19, 2018 (IN) .............................. 201821043440

(51) Int. Cl.
*A61B 5/00* (2006.01)
*G16Y 40/10* (2020.01)
*G16Y 40/35* (2020.01)
*G06K 9/00* (2006.01)

(52) U.S. Cl.
CPC ........ *A61B 5/6804* (2013.01); *G06K 9/00335* (2013.01); *G16Y 40/10* (2020.01); *G16Y 40/35* (2020.01)

(58) Field of Classification Search
CPC ...... A61B 5/6804; G16Y 40/10; G16Y 40/35; G06K 9/00335; G06F 3/017; G06F 1/163; G06F 3/0488; G06F 2203/04104; G06F 21/316; G06F 3/01

USPC ....................................................... 340/573.1
See application file for complete search history.

(56) References Cited

U.S. PATENT DOCUMENTS

| | | | |
|---|---|---|---|
| 7,633,076 B2 | 12/2009 | Huppi et al. | |
| 9,662,015 B2 | 5/2017 | Proud et al. | |
| 9,693,592 B2 * | 7/2017 | Robinson | A41D 31/04 |
| 9,933,908 B2 * | 4/2018 | Poupyrev | G06F 3/0446 |
| 9,983,747 B2 * | 5/2018 | Poupyrev | G06F 3/0416 |
| 10,088,908 B1 * | 10/2018 | Poupyrev | G06F 3/017 |
| 10,268,321 B2 * | 4/2019 | Poupyrev | G06F 3/0445 |
| 2012/0156926 A1 * | 6/2012 | Kato | D03D 15/587 439/502 |

(Continued)

FOREIGN PATENT DOCUMENTS

CN 104298352 1/2015

*Primary Examiner* — Eric Blount
(74) *Attorney, Agent, or Firm* — Finnegan, Henderson, Farabow, Garrett & Dunner, LLP

(57) ABSTRACT

This disclosure relates generally to a system and method for analyzing live activity on the conductive fabrics with intelligent touch. The system comprises a plurality of modules and these modules are in sync with the processor of the system to take action based on a plurality of instructions of the memory. Further, the system comprises fabrics, which are of conductive in nature, are used as a conductive touch pads for inputs to the system. The input data from touch pads are analyzed to determine pattern of actions. These patterns are associated with the IoT devices and the system uses them to trigger at least one action on the at least one IoT device based on a predefined training data set.

6 Claims, 3 Drawing Sheets

(56) References Cited

U.S. PATENT DOCUMENTS

| | | | |
|---|---|---|---|
| 2014/0070957 A1* | 3/2014 | Longinotti-Buitoni | G06F 3/011 340/870.01 |
| 2015/0370320 A1* | 12/2015 | Connor | A61B 5/1126 345/173 |
| 2016/0038083 A1* | 2/2016 | Ding | A61B 5/1121 600/388 |
| 2016/0283101 A1* | 9/2016 | Schwesig | A41D 1/002 |
| 2017/0060298 A1* | 3/2017 | Hwang | G06F 3/044 |
| 2017/0325518 A1* | 11/2017 | Poupyrev | A41D 1/005 |
| 2018/0160943 A1* | 6/2018 | Fyfe | A61B 5/14542 |
| 2018/0310659 A1* | 11/2018 | Poupyrev | A61B 5/04085 |
| 2019/0090812 A1* | 3/2019 | Martin | A61B 5/0205 |
| 2020/0186605 A1* | 6/2020 | Rakshit | H04L 67/10 |
| 2020/0237031 A1* | 7/2020 | Daniels | A61B 5/02055 |

* cited by examiner

SYSTEM AND METHOD FOR ANALYZING USER'S ACTIVITIES ON CONDUCTIVE FABRICS TO TRIGGER IOT DEVICES

CROSS-REFERENCE TO RELATED APPLICATIONS AND PRIORITY

This U.S. patent application claims priority under 35 U.S.C. § 119 to India Application No. 201821043440, filed on Nov. 19, 2018. The entire contents of the abovementioned application are incorporated herein by reference.

TECHNICAL FIELD

The present subject matter described herein, in general, relates to an intelligent system to understand requirement of activity on fabrics, more particularly, systems and methods to analyze one or more activities on the fabrics and to trigger at least one internet of things (IoT) device based on the activities.

BACKGROUND

Currently there is a very limited possibility for humans to interact with the fabrics. It has always been to have an extra device to control and monitor any activity. Existing systems do not have any embedded device on the fabrics, which can intelligently help elderly and physically challenged person to interact with the external environment in a smart manner. Smart fabric with intelligent gesture mapping would be able to bring any desire of the human to enable the world of opportunities. The intelligent gesture mapping on the fabrics would help to interact, immerse and observe the IoT world with a larger ecosystem.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In one embodiment of the disclosure, a system for analyzing one or more activities of a user on conductive fabrics to trigger at least one internet of things (IoT) device, the system comprising a memory storing a plurality of set of instructions, one or more hardware processors communicatively coupled with the memory, wherein the one or more hardware processors are configured by instructions to execute one or more modules. Further the system comprising a receiving module configured to receive at least one instruction from the user, wherein the instruction received is in the form of a gesture of the user, wherein the instruction includes usage instruction associated with the at least one IoT device, an analyzing module configured to analyze the received at least one instruction to determine at least one pattern of action associated with at least one IoT device and a triggering module configured to trigger at least one action on the at least one IoT device based on the determined pattern of action of each IoT device and a predefined training data set. It would be appreciated that the conductive fabrics comprising a plurality of silver thin wires, wherein the plurality of silver thin wires are integrated into thread to make a cloth. Further, the conductive fabrics has a predefined low resistance. It is to be noted that the predefined training data set comprises of one or more gesture patterns, one or more gesture inputs and one or more gesture interactions on the surface of the conductive fabrics.

In another embodiment of the disclosure, a method for analyzing one or more activities of a user on conductive fabrics to trigger at least one internet of things (IoT) device. The method comprising one or more steps such as receiving at least one instruction from the user, wherein the instruction received is in the form of a gesture of the user, wherein the instruction includes usage instruction associated with the at least one IoT device, analyzing the received at least one instruction to determine at least one pattern of action associated with at least one IoT device and triggering at least one action on the at least one IoT device based on the determined pattern of action of each IoT device and a predefined training data set. It would be appreciated that the conductive fabrics comprising a plurality of silver thin wires, wherein the plurality of silver thin wires are integrated into thread to make a cloth. Further, the conductive fabrics has a predefined low resistance. It is to be noted that the predefined training data set comprises of one or more gesture patterns, one or more gesture inputs and one or more gesture interactions on the surface of the conductive fabrics.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes, which may be substantially represented in computer readable medium and so executed by a computing device or processor, whether or not such computing device or processor is explicitly shown.

BRIEF DESCRIPTION OF THE DRAWINGS

The embodiments herein will be better understood from the following detailed description with reference to the drawings, in which.

DETAILED DESCRIPTION OF EMBODIMENTS

Figure 1:
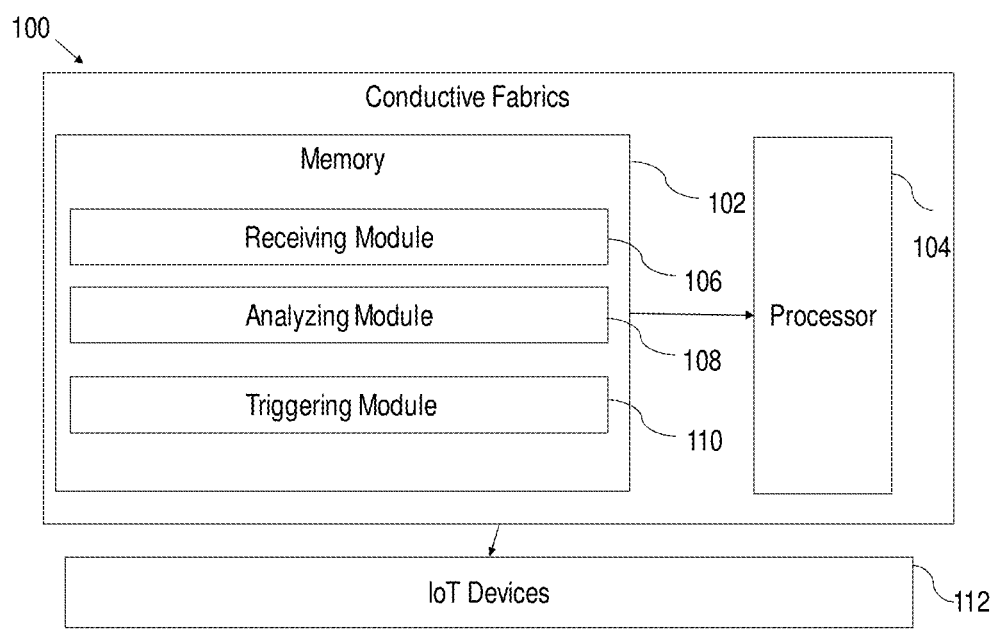
FIG. 1 is a block diagram showing a system for analyzing one or more activities of a user on fabrics to trigger one or more IoT devices, according to an embodiment of the present disclosure.

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to enable those of skill in the art to practice the embodiments herein. Accordingly, the examples should not be construed as limiting the scope of the embodiments herein.

Some embodiments of this invention, illustrating all its features, will now be discussed in detail. The words "comprising," "having," "containing," and "including," and other forms thereof, are intended to be equivalent in meaning and be open ended in that an item or commodities following any one of these words is not meant to be an exhaustive listing of such item or commodities, or meant to be limited to only the listed item or commodities.

It must also be noted that as used herein and in the appended claims, the singular forms "a," "an," and "the" include plural references unless the context clearly dictates otherwise. Although any systems and methods similar or equivalent to those described herein can be used in the practice or testing of embodiments of the present invention, the preferred, systems and methods are now described. In the following description for the purpose of explanation and understanding, reference has been made to numerous embodiments for which the intent is not to limit the scope of the invention.

One or more components of the invention are described as module for the understanding of the specification. For example, a module may include self-contained component in a hardware circuit comprising of logical gate, semiconductor device, integrated circuits or any other discrete component. The module may also be a part of any software program executed by any hardware entity for example processor. The implementation of module as a software program may include a set of logical instructions to be executed by a processor or any other hardware entity.

The disclosed embodiments are merely exemplary of the invention, which may be embodied in various forms. The elements illustrated in the Figures interoperate as explained in more detail below. Before setting forth the detailed explanation, however, it is noted that all of the discussion below, regardless of the particular implementation being described, is exemplary in nature, rather than limiting. For example, although selected aspects, features, or components of the implementations are depicted as being stored in memories, all or part of the systems and methods consistent with the attrition warning system and method may be stored on, distributed across, or read from other machine-readable media.

The embodiments herein provide a system and method for analyzing one or more activities of a user on fabrics to trigger at least one IoT device. The system comprises a plurality of modules in sync with a processor of the system to perform one or more actions based on one or more instructions stored in the memory. It receives at least one activity of the user on the fabric. It is to be noted that the raw data may comprise of wrong triggers to IoT devices, therefore the received activities are analyzed to determine at least one pattern of action for triggering at least one action at one IoT device.

Referring FIG. 1, a system (100) for analyzing one or more activities of a user on fabrics to trigger at least one IoT device. The system (100) includes a memory (102) storing a plurality set of instructions, one or more processors (104), wherein the one or more processors (104) are communicatively connected with memory (102) to execute the plurality set of instructions of the memory (102). Further, the system (100) comprising a receiving module (106) configured to receive at least one instruction from a user, an analyzing module (108) configured to analyze the received instruction to determine at least one pattern of action, and a triggering module (110) configured to trigger at least one action at the at least one IoT device (112) based on the determined at least one pattern of action and a predefined training data set.

In the preferred embodiment of the disclosure, the receiving module (106) is configured to receive at least one instruction from a user as an input to the system (100). It would be appreciated that the received instruction is in a form of gesture of the user. The received at least one instruction includes usage instructions of the one or more IoT devices within the predefined environment.

Figure 2:
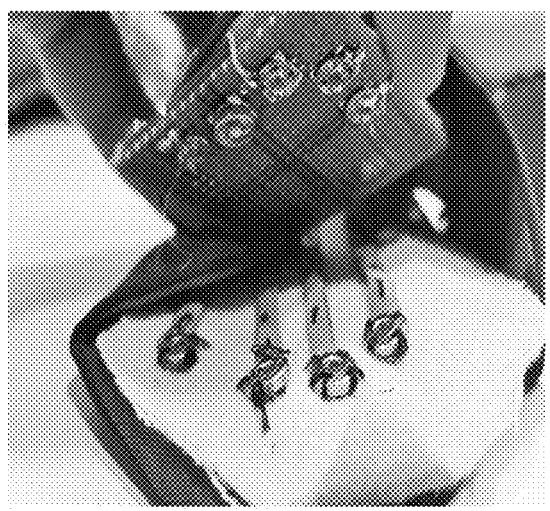
FIG. 2 is a schematic diagram showing a system for analyzing one or more activities of a user on a tie to trigger IoT devices according to an embodiment of the present disclosure.
Figure 2:
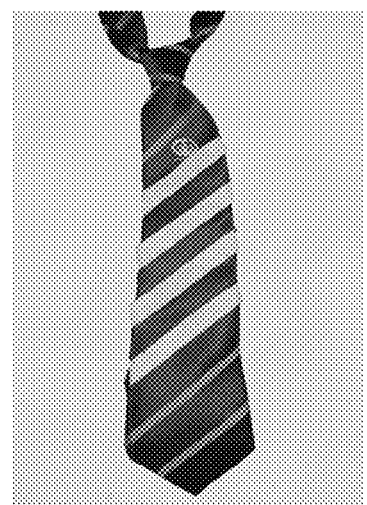

In one example, wherein during presentation a user/presenter usually takes help of keyboard to change slides, but having a USB HID (human interface device) profile connected with a keyboard to personal computer, he does not require any external driver. The user can have the system along with his/her tie or other cloths as suitable or of him/her choice as shown in FIG. 2. It is to be noted that the system (100) is integrated with a conductive fabric to make the conductive fabric smarter and the user can change slides by gestures only.

It is to be noted that the conductive fabrics has silver thin wires, which are integrated into thread to make a cloth for user. The conductive fabrics comprises means for connecting the user through at least one touch point of the conductive fabrics to the at least one IoT device. Further, the user can also control other IoT devices and report various sensor data like temperature.

In the preferred embodiment of the disclosure, the analyzing module (108) is configured to analyze the received at least one instruction from the user to determine at least one pattern of action. It is to be noted that the determined at least one pattern of action to be used to trigger at least one action through a node at the at least IoT device (112). It would be appreciated that the node at the at least one IoT device (112) may be a hardware or a combination of both hardware and software.

In the preferred embodiment of the disclosure, the triggering module (110) is configured to trigger at least one action at the at least one IoT device (112) based on the determined a predefined training data set. It would be appreciated that the training dataset comprises of gesture patterns, gesture inputs and gesture interactions on the surface. Moreover, there is also a live learning performed for new command inputs from the set of gesture interactions being defined.

Figure 3:
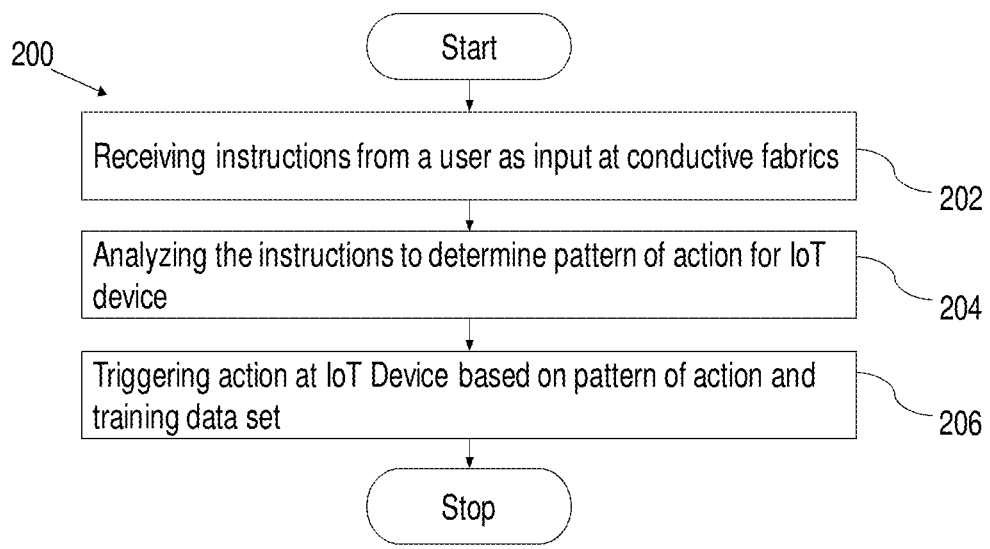
FIG. 3 is a flow diagram showing a method for analyzing one or more activities of a user on fabrics to trigger one or more IoT devices according to an embodiment of the present disclosure.

Referring FIG. 3, which illustrates a flowchart (200) for analyzing the one or more activities of a user on conductive fabrics to trigger at least one IoT device (112).

In the preferred embodiment of the disclosure, initially at the step (202), at least one instruction of the user is received on the conductive fabrics. Wherein, the at least one instruction is in a form of a gesture of the user. The received at least one instruction includes usage instructions associated with the at least one IoT device. It would be appreciated that the conductive fabrics has silver thin wires, which are integrated into thread to make a cloth for the user. The conductive fabrics comprises means for connecting the user through at least one touch point of the conductive fabrics to the at least one IoT device. Further, the user can also control other IoT devices and report various sensor data like temperature.

In the preferred embodiment of the disclosure, at the step (204), the received at least one instruction is analyzed to determine the at least one pattern of action associated with the at least one IoT device. It would be appreciated that the at least one pattern of action to be used to trigger an action through a node at each IoT device. It is to be noted that the node at the at least one IoT device may be a hardware or a combination of both hardware and software.

In the preferred embodiment of the disclosure, at the last step (206), wherein at least one action is triggered at the at least one IoT device based on the determined at least one pattern of action and a predefined training data set. It would be appreciated that the predefined training data set comprises of gesture patterns, gesture inputs and gesture interactions on the surface. Moreover, there is also a live learning performed for new command inputs from the set of gesture interactions being defined.

The embodiments of present disclosure herein addresses an unresolved problem of any arrangement of embedded devices on the fabrics, which can intelligently interact with IoT devices in the external environment in a smart manner. The embodiments herein, thus provides a system and method for analyzing one or more activities of a user on fabrics to trigger at least one action on the at least one IoT device. The system comprises a plurality of modules in sync with a processor of the system to perform one or more actions based on one or more instructions stored in the memory. It receives at least one activity of the user on the fabric. It is to be noted that the raw data may comprise of wrong triggers to one or more IoT devices, therefore the received activities are analyzed to determine at least one pattern of action for triggering at least one action at the IoT device.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device, which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device, which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A system for analyzing one or more activities of a user on conductive fabrics to trigger at least one internet of things (IoT) device, the system comprising:
   a memory storing a plurality of set of instructions;
   one or more hardware processors communicatively coupled with the memory, wherein the one or more hardware processors are configured by instructions to execute one or more modules comprising:
   a receiving module configured to receive at least one instruction from the user on the conductive fabrics, wherein the instruction received is in the form of a gesture of the user, wherein the instruction includes usage instruction associated with the at least one IoT device, and wherein the conductive fabrics has a predefined low resistance;
   an analyzing module configured to analyze the received at least one instruction to determine at least one pattern of action associated with at least one IoT device; and
   a triggering module configured to trigger at least one action on the at least one IoT device based on the determined pattern of action through a node at the at least IoT device and a predefined training data set, wherein the predefined training data set comprises one or more gesture interactions on a surface of the conductive fabrics, and wherein the triggering module dynamically learns new command inputs from a set of defined gesture interactions.

2. The system of claim 1, wherein the conductive fabrics comprising a plurality of silver thin wires, wherein the plurality of silver thin wires are integrated into thread to make a cloth.

3. A method for analyzing one or more gesture activities of a user on conductive fabrics to trigger at least one internet of things (IoT) device, the method comprising one or more steps of:
- receiving at least one instruction from the user on conductive fabrics, wherein the instruction received is in a form of a gesture of the user, wherein the instruction includes usage instruction associated with at least one IoT device, and wherein the conductive fabrics has a predefined low resistance;
- analyzing the received at least one instruction to determine at least one pattern of action associated with the at least one IoT device; and
- triggering at least one action at the at least one IoT device based on the determined pattern of action through a node at the at least IoT device and a predefined training data set, wherein the predefined training data set comprises one or more gesture interactions on a surface of the conductive fabrics, and wherein the triggering module dynamically learns new command inputs from a set of defined gesture interactions.

4. The method of claim 3, wherein the conductive fabrics comprising a plurality of silver thin wires, wherein the plurality of silver thin wires are integrated into thread to make a cloth.

5. A non-transitory computer readable medium storing one or more instructions which when executed by a processor on a system, cause the processor to perform method analyzing one or more gesture activities of a user on conductive fabrics to trigger at least one internet of things (IoT) device comprising:
- receiving at least one instruction from the user on conductive fabrics, wherein the instruction received is in a form of a gesture of the user, wherein the instruction includes usage instruction associated with at least one IoT device, and wherein the conductive fabrics has a predefined low resistance;
- analyzing the received at least one instruction to determine at least one pattern of action associated with the at least one IoT device; and
- triggering at least one action at the at least one IoT device based on the determined pattern of action through a node at the at least IoT device and a predefined training data set, wherein the predefined training data set comprises one or more gesture interactions on a surface of the conductive fabrics, and wherein the triggering module dynamically learns new command inputs from a set of defined gesture interactions.

6. A non-transitory computer readable medium of claim 5, wherein the conductive fabrics comprising a plurality of silver thin wires, wherein the plurality of silver thin wires are integrated into thread to make a cloth.

* * * * *